United States Patent
Kim et al.

(10) Patent No.: US 9,238,016 B2
(45) Date of Patent: Jan. 19, 2016

(54) ANTIBIOTIC COMPOSITION COMPRISING FLUFENAMIC ACID AS AN ACTIVE INGREDIENT

(75) Inventors: Kyeong Kyu Kim, Seoul (KR); Sung Wook Kang, Suwon-si (KR)

(73) Assignee: SUNGKYUNKWAN UNIVERSITY FOUNDATION FOR CORPORATE COLLABORATION, Suwon-Si (KR)

( * ) Notice: Subject to any disclaimer, the term of this patent is extended or adjusted under 35 U.S.C. 154(b) by 25 days.

(21) Appl. No.: 13/522,764

(22) PCT Filed: Jan. 21, 2011

(86) PCT No.: PCT/KR2011/000444
§ 371 (c)(1),
(2), (4) Date: Oct. 9, 2012

(87) PCT Pub. No.: WO2011/090345
PCT Pub. Date: Jul. 28, 2011

(65) Prior Publication Data
US 2013/0143856 A1    Jun. 6, 2013

(30) Foreign Application Priority Data
Jan. 22, 2010 (KR) ........................ 10-2010-0006217

(51) Int. Cl.
*A61K 31/195* (2006.01)
*A61K 31/196* (2006.01)
*A61K 31/495* (2006.01)
*A61K 45/06* (2006.01)

(52) U.S. Cl.
CPC ............. *A61K 31/195* (2013.01); *A61K 31/196* (2013.01); *A61K 31/495* (2013.01); *A61K 45/06* (2013.01)

(58) Field of Classification Search
CPC .......................... A61K 31/165; A61K 31/196
See application file for complete search history.

(56) References Cited

U.S. PATENT DOCUMENTS 4,024,279 A * 5/1977 Zor et al. ....................... 514/567
2005/0014729 A1 * 1/2005 Pulaski ......................... 514/165

FOREIGN PATENT DOCUMENTS

KR          10-0759988 B1    9/2007
KR    10-2008-0008321 A    1/2008

OTHER PUBLICATIONS

Lowder, Bethan V., et al., "Recent human-to-poultry host jump, adaptation, and pandemic spread of *Staphylococcus aureus*,"PNAS, Nov. 17, 2009, pp. 19545-19550, vol. 106, No. 46.
GenBank Accession ACY10586, aldo/keto reductase family [Staphy10coccus aureus subsp. 8-10 aureus ED98], Oct. 27, 2009, Web URL: http://www.ncbi.nlm.nih.gov/protein/ACY10586.
GenBank Accession ACY11686, aldo/keto reductase family [Staphy10coccus aureus subsp. 8,9,11 aureus ED98], Oct. 27, 2009, Web URL: http://www.ncbi.nlm.nih.gov/protein/ACY11686.
GenBank Accession ACY12095, aldo/keto reductase family [Staphy10coccus aureus subsp. 8,9,12 aureus ED98], Oct. 27, 2009 Web URL: http//www.ncbi.nlm.nih.gov/protein/ACY12095.

* cited by examiner

*Primary Examiner* — Wu-Cheng Winston Shen
*Assistant Examiner* — Christopher R Stone
(74) *Attorney, Agent, or Firm* — NSIP Law

(57) ABSTRACT

The present invention relates to a novel antibiotic, and more specifically relates to an antibiotic composition comprising flufenamic acid as an active ingredient, which can reduce drug toxicity and side effects and the problem of antibiotic resistance caused by excessive use of antibiotics since the composition exhibits a good therapeutic effect, even in a small dose, when it is administered either alone or together with another antibiotic of the prior art.

12 Claims, 9 Drawing Sheets

Fig. 1 Flufenamic acid

Fig. 5

```
AKR1C3    MDSKQQCVKLNDGHFMPVLGFGTYAPPEVPRSKALEVTKLAIEAGFRHIDSAHLYNNEEQ
SA0658    --MLNEIQILNNGYPMPSVGLGVYKIS---DEDMTKVVNAAIDAGYRAFDTAYFYDN  S
SA1606    ----MEVKTFYNGNTMPQIGLGTFRVEN--DENCMESVKYAIEQGYRSIDTAKVYGNEEQ
SA2001    ----MNHIEISKDVKIPVLGFGVFQIPQ---EQTAEAVKEAIKAGYRHIDTAQSYLNETE
                 :    :..  :*  :*:*.:       ..  :  .:  **. *:* :*:*   * ** .

AKR1C3    VGLAIRSKIADGSVKREDIFYTSKLWSTFHRPELVRPALENSLKKAQLDYVDLYLIHSPM
SA0658    LGR----ALKDNGVDREDLFITTKLWNDYQGYEKTFEYFNKSIENLQTDYLDLFLIHWPC
SA1606    VGAGIRAGLESTGIAREDLFITSKLYFEDFGRENVAAAYEASLSRLGLKYLDLYLVHWPG
SA2001    VGQG----IEASGIDRSELFITTKVWIENVNYEDTIKSIERSLQRLNLDYLDLVLIHQPY
          :*           :    .:  *.:;*  *:;*::        *  .    : *:..   .*:** *;* *

AKR1C3    SLKPGEELSPTDENGKVIFDIVDLCTTWEAMEKCKDAGLAKSIGVSNFNRRQLEMILNKP
SA0658    EADG----------------LFLETYKAMEELYEQGKVKAIGVCNFNVHHLEKLMAQS
SA1606    TNEA----------------VMVDTWKGMEDLYKNNKAKNIGVSNFEPEHLEALLAQV
SA2001    NDVYG----------------SWRALEELKENGKIKAIGVSNFGVDRIVDLGIHN
                                 :;.,:*.   ..   *  ***,**   ::   :   :

AKR1C3    GLKYKPVCNQVECHPYFNRSKLLDFCKSKDIVLVAYSALGSQRDKRWVDPNSPVLLEDPV
SA0658    SIK--P  VNQIEVEPYFNQQELQEFCDRHDIKVTAWMPLMR---------NRGLLDNPV
SA1606    SIK--PVINQVEYHPYLTQHKLKLYLAAQHIVMESWSPL-----------NAQILNDET
SA2001    QIQ--PQVNQIEINPFHQQEEQVAALQQENVVVEAWAPFAE---------GKNQLFQNQL
          ::    *   **;* ;*:   : :       ..: : :/ .:            .  ::::

AKR1C3    LCALAKKHKRTPALIALRYQLQRGVVVIAKSYNEQRIRQNVQVFEFQLTAEOMKAIDGLD
SA0658    IVKIAEKYHKTPAQVVLRWHLAHNRIIIPKSQTPKRIQENIDILDFNLELTEVAEIDALD
SA1606    IKDIAQELGKSPAQVVLRWNVQHGVVIIPKSVTPNRISENFQIFDFELSDEQMTRIDGLN
SA2001    LQAIADKYNKSIAQVILRWLVERDIVVLAKSVNPERMAQNLDIFDFELTEEDKQQIATLE
          :   :*.:    ::  *  :  **:   :  .  :::,**  .  ;*:  :*.:::::*:*    :   *  *:

AKR1C3    RNLHYFNSDSFASHPNYPYSDEYLEHHHHHH
SA0658    R------NARQGKNPDDVKIGDLK------
SA1606    Q------DKRIGPDPKTFEG----------
SA2001    ES-----NSQFFSHADPEMIKALTSRELDV-
                    .        .      ...
```

Fig. 9
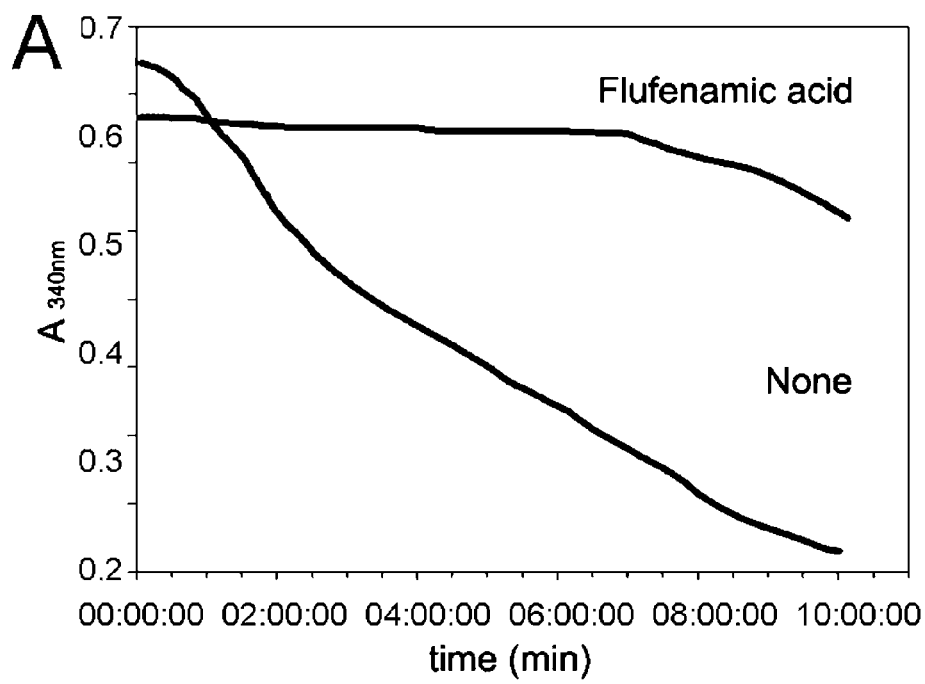
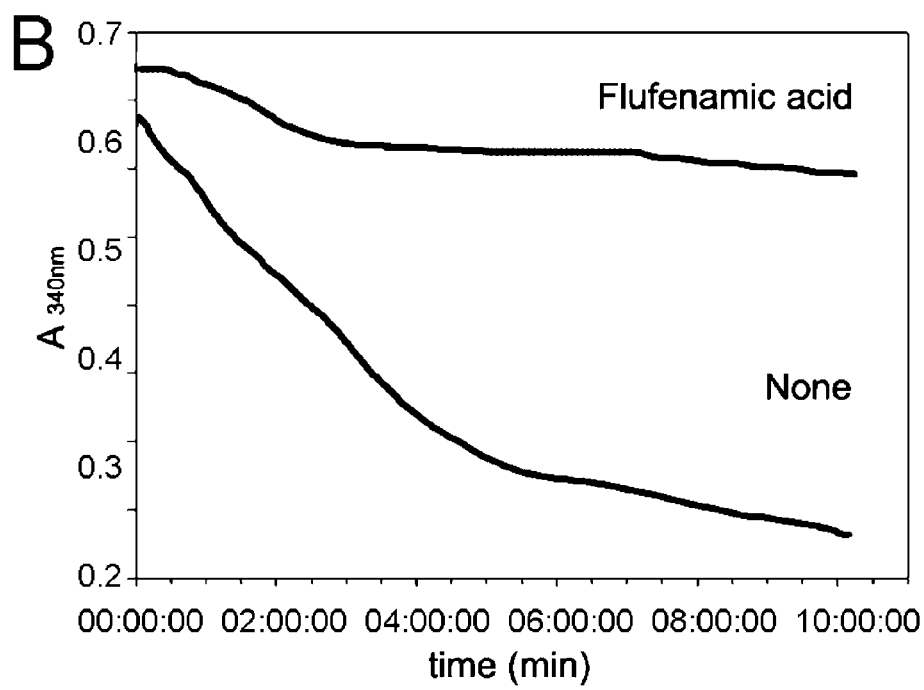

ANTIBIOTIC COMPOSITION COMPRISING FLUFENAMIC ACID AS AN ACTIVE INGREDIENT

CROSS REFERENCE TO RELATED APPLICATION

This application is a National Stage of International Application No. PCT/KR2011/000444, filed on Jan. 21, 2011, claiming priority based on Korean Patent Application No. 10-2010-0006217, filed Jan. 22, 2010, the contents of all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 7, 2013, is named 042099.0001_SL.txt and is 11,516 bytes in size.

TECHNICAL FIELD

The present invention is to provide a novel antibiotic material effective for killing or inhibiting the growth or metabolism of Gram-positive bacteria.

BACKGROUND ART

Gram staining is a method of differentiating bacterial species into two large groups which are the Gram-positive and Gram-negative bacteria, which was devised by Danish physician H. C. J. Gram (1853-1938) in 1884 not for the purpose of distinguishing one type of bacterium from another but to enable bacteria to be more visible in stained sections. These bacterial groups are generally different in various aspects including sensitivity to chemical agents, nutrients necessary for their growth, response to physical and chemical stimuli, toxins produced thereby, and lesions caused thereby. Representative among Gram-positive bacteria, characterized by a purple color stain, are *Staphylococcus* spp., *Pneumococcus* spp, *Mycobacterium leprae, Corynebacterium diphtheria, Clostridium tetani, Bacillus anthracis*, and *Actinomyces*. Most of these bacteria are leading pathogens responsible for serious disease such as diphtheria, tuberculosis, pneumonia, etc.

For example, *Staphylococcus aureus*, a Gram-positive bacterium, is a pathogen which causes various diseases including food poisoning, impetigo, cellulitis, scalded skin syndrome, mastitis, bacteremia, sepsis, *staphylococcal* pneumonia, endocarditis, heart failure, osteomylitis, *Staphylococci sepsis*, circulatory collapse, and toxic shock syndrome. In the United States, *staphylococcal* infection is diagnosed in more than two million people every year and accounts for the death of more than ninety thousand people.

Most bacterial infections are readily cured by antibiotics such as penicillin, etc., but some have recently been reported to be difficult to treat. Bacteria become resistant to antibiotic drugs through a spontaneous DNA mutation or the uptake of foreign DNA so that they are able to survive exposure to an antibiotic. This situation is called "antibiotic resistance" and the bacteria with antibiotic resistance are called "drug resistant bacteria." In addition, drug-resistant bacteria show multidrug resistance in which, for example, only 10% and 50% of them can be regulated with penicillin and methicillin, respectively.

Antibiotic resistance has been found over a broad spectrum of Gram-positive pathogenic bacteria including *Staphylococcus, Streptococcus, Entracoccus, Bacillus* and *Listeria*. Of them, MRSA (Methicillin-Resistant *Staphylococcus Aureus*), VRSA (Vancomycin-Resistant *Staphylococcus Aureus*), MRE (multiple-drug resistant enterococci) and VRE (Vancomycin-Resistant enterococci) attract social interest because they are more dangerous.

For example, MRSA is treated with vancomycin, more potent than methicillin, but some show resistance to the drug, as well. Because such resistant pathogens are poor in susceptibility to drugs, it is often necessary to apply a large dose of antibiotics which is, however, noxious to the patient. In recent years, the increasing spread of drug resistance by *S. aureus* has been recognized as serious threat to the health of mankind. Therefore, there is a pressing need for a novel antibiotic that works through a new mechanism that confers a potent therapeutic effect even at a small dose thereof on an infection of the drug-resistant *S. aureus*.

Classically, new antibiotics have been developed by chemically modifying bioactive compounds produced by microorganisms. With the great progress of genomic and drug discovery techniques such as high-throughput screening, many new drug targets are secured from which various drug candidates have been separated. The time and cost which it takes for such new drug candidates to undergo clinical trials and to acquire the approval of the FDA is currently acting as the main hindrance to the development of novel drugs. Hence, if found, new uses of commercially available drugs which have passed clinical trials and have had their safety verified in vivo will provide the advantage of significantly reducing the time and cost required to bring novel drugs to market.

Given this background, the present inventors have searched for finding a drug that works in a manner different from already known antibiotic mechanisms in the art in order to overcome the problem with multidrug resistance and, in addition, for finding a compound that exhibits antibiotic activity from among drugs currently used in clinics in order to make it easier to develop a novel antibiotic agent.

DISCLOSURE

Technical Problem

The present invention is intended to provide a novel antibiotic destructive of or inhibitory of the growth or metabolism of Gram-positive bacteria which does not confer drug resistance on the bacteria but is effective on drug resistant bacteria, and to reduce the time and cost taken for the development of a novel antibiotic by taking advantage of a preexisting drug currently used in clinics. More particularly, the present invention provides an antibiotic composition with potent inhibitory activity against Gram-positive bacteria, comprising flufenamic acid.

Technical Solution

The present invention newly discovers the use of flufenamic acid, currently used for anti-inflammation, as a novel antibiotic in the treatment of bacterial infections. More particularly, the present invention provides an antibiotic composition comprising flufenamic acid, a derivative thereof, an isomer thereof, or a salt thereof as an active ingredient, and various uses thereof, that is, a pharmaceutical or cosmetic composition with antibiotic activity.

In addition, the present invention is directed to an aldo-keto reductase, present in Gram-positive bacteria, which can be utilized as a target protein of an antibiotic for destroying or inhibiting the growth or metabolism of Gram-positive bacteria.

Leading to the present invention, intensive and thorough research was done regarding an antibiotic which has a working mechanism that is different from classical antibiotics. This research resulted in the finding that flufenamic acid, currently used as an analgesic, can inhibit the growth and metabolism of Gram-positive bacteria through a novel antibiotic mechanism.

Below, a detailed description will be given of the present invention.

The present invention addresses an antibiotic composition comprising flufenamic acid, flufenamic acid derivative, flufenamic acid isomer, or flufenamic acid salt as an active ingredient.

In the present invention, flufenamic acid is used to regulate the growth or metabolism of Gram-positive bacteria, that is, it has potent inhibitory activity against Gram-positive bacteria.

No special limitations are imparted to species of the Gram-positive bacteria against which the antibiotic composition of the present invention exhibits inhibitory activity. Preferred examples include *Staphylococcus aureus, Staphylococcus epidermidis, Bacillus subtilis, Listeria monocytogenes,* and *Enterococcus faecium*. More preferred is mithicillin-resistant *Staphylococcus aureus* (MRSA).

Particularly, the present invention relates to an antibiotic composition with potent destructive and inhibitory activity against drug-resistant bacteria, comprising flufenamic acid as an active ingredient. Included among the drug-resistant bacteria are MRSA (Methicillin-Resistant *Staphylococcus aureus*), VRSA (Vancomycin-Resistant *Staphylococcus Aureus*), MRE (multiple-drug resistant enterococci) and VRE (Vancomycin-Resistant enterococci).

Any flufenamic acid, whether naturally occurring or artificially synthesized, may be used in the present invention. If artificially synthesized, flufenamic acid may be prepared from any material using any method. For example, flufenamic acid may be synthesized through substitution and fraction (Herbert O. House: Modern Synthetic Reactions, $2^{nd}$ ED., The Benjamin/Cummings Publishing Co., 1972).

Instead of flufenamic acid, flufenamic acid derivative, flufenamic acid isomer, or flufenamic acid salt may be used as an active ingredient of the composition according to the present invention.

It is naturally understood that all stereoisomers, diastereomers, enantiomers, and racemates of flufenamic acid fall within the scope of the present invention.

The salt of flufenamic acid useful in the present invention may be an acid salt or a base salt. By way of example, pharmaceutically acceptable salts of flufenamic acid include sodium, calcium and potassium salts for the hydroxy group and hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) for the amino group, but are not limited thereto. They may be prepared using methods or techniques well known in the art.

flufenamic acid, flufenamic acid derivative, flufenamic acid isomer, or flufenamic acid salt act as an active ingredient in the antibiotic composition provided by the present invention, targeting the aldo-keto reductase of Gram-positive bacteria.

As stated above, flufenamic acid inhibits the activity of aldo-keto reductase in Gram-positive bacteria. For example, the aldo-keto reductase which flufenamic acid target may be the enzymes present in *Staphylococcus aureus*, and may preferably be SA0658, SA1606 or SA2001.

In one embodiment of the present invention, the antibiotic composition may further comprise a conventional antibiotic against Gram-positive bacteria in addition to flufenamic acid, flufenamic acid derivative, flufenamic acid isomer, or flufenamic acid salt thereof. So long as it is approved for use in the treatment of the infection of Gram-positive bacteria, any conventional antibiotic may be employed in the composition of the present invention. Preferred is norfloxacin, oxacillin or cephalothin.

Also, the present invention addresses a Gram-positive bacterial aldo-keto reductase as a target protein of an antibiotic that is destructive or inhibitory of the growth or metabolism of Gram-positive bacteria.

The Gram-positive bacteria affected by the present invention are not limited specifically to species so long as they contain aldo-keto reductase therein. Preferred examples include *Staphylococcus aureus, Staphylococcus epidermidis, Bacillus subtilis, Listeria monocytogenes* and *Enterococcus faecium*. More preferred is methicillin-resistant *S. aureus* (MRSA).

In the present invention, the aldo-keto reductase functions as a target protein on which an inhibitory agent acting against the growth or metabolism of Gram-positive bacteria directly acts.

No particular limitations are imposed on the kinds of the inhibitory agent, whether natural or synthetic. The aldo-keto reductase which is regulated by the inhibitory agent may be an enzyme which is found in Gram-positive bacteria.

For example, the aldo-keto reductase may be found in *Staphylococcus aureus* and preferably SA0658 with the amino acid sequence of SEQ ID NO: 1, SA1606 with the amino acid sequence of SEQ ID NO: 2 or SA2001 with the amino acid sequence of SEQ ID NO: 3.

Further, the present invention addressed an antibiotically active, pharmaceutical composition comprising flufenamic acid, flufenamic acid derivative, flufenamic acid isomer, or flufenamic acid salt as an active ingredient.

Showing inhibitory activity against Gram-positive bacteria without side effects and toxicity in the body, the composition is useful for preventing and treating diseases caused by Gram-positive bacteria. No particular limitations are imparted on the type of inhibition exhibited against Gram-positive bacteria. Preferably, it destroys or inhibits the growth or metabolism of Gram-positive bacteria.

The pharmaceutical composition of the present invention may be administered orally or parenterally to mammals such as rats, dogs, domestic animals, and humans. For example, it may be administered orally or injected intrarectally, intramuscularly or subcutaneously, or via the route of the dura mater within the uterine or via a cerebrovascular route. Preferable are parenteral routes, with greater preference for transdermal administration. Thus, the composition may be applied topically.

For practical use in the destruction or inhibition of growth or metabolism of Gram-positive bacteria, the composition in accordance with the present invention may be formulated into typical forms, for example, oral dosage forms such as tablets, capsules, troches, liquids, suspensions, etc., injection forms such as injectable solutions or suspensions, powder that can be reconstituted with distilled water for injection, and ready-to-use solutions, topical forms such as ointments, creams, lotions, liquids, sprays, etc.

So long as it is pharmaceutically accepted, any vehicle may be used for formulating the composition of the present invention. By way of example, the composition may be formulated with a binder, a suspension agent, a disintegrant, an excipient, a solubilizer, a dispersant, a stabilizer, a colorant, and/or a flavorant for oral dosage forms, or with a preservative, an appeaser, a solubilizer and/or a stabilizer for injection forms, or with a base, an excipient, a lubricant, a preservative and/or a propellant for topical forms. The pharmaceutical formulations thus prepared may be administered orally or applied topically.

The effective dosage of the pharmaceutical composition in accordance with the present invention depends on various factors, including dosage form, the patient's age, weight, gender, state of health, diet, the time of administration, the route of administration, excretion rate, sensitivity, etc. In general, it may be administered in a single dose or in multiple doses per day at a daily dose ranging from 0.01 to 200 mg/day and preferably at a daily dose ranging from 5 to 50 mg/kg.

The antibiotically active, pharmaceutical composition comprising flufenamic acid, flufenamic acid derivative, flufenamic acid isomer, or flufenamic acid salt in according to the present invention may further comprise an antibiotic inhibitory of Gram-positive bacteria. Any antibiotic, if approved for use in inhibiting Gram-positive bacteria, may be used in the composition of the present invention. Preferred examples of the antibiotic include norfloxacin, oxacillin and cephalothin, but are not limited thereto.

In addition, the present invention addresses an antibiotically active, cosmetic composition comprising flufenamic acid, flufenamic acid derivative, flufenamic acid isomer, or flufenamic acid salt.

The cosmetic composition may further comprise an additive in addition to flufenamic acid as an active ingredient. The additive, if conventionally used, may be contained in the cosmetic composition. For example, a supplement and an excipient such as an antioxidant, a stabilizer, a solubilizer, vitamin, a colorant, a flavorant, etc. may be used. In the cosmetic composition, a transdermal delivery enhancer may be employed.

The composition of the present invention may contain flufenamic acid, flufenamic acid derivative, flufenamic acid isomer, or flufenamic acid salt in an amount of from 0.0001 to 99 wt %, and preferably in an amount of from 0.001 to 90 wt %.

The cosmetic composition of the present invention may be prepared into any conventional formulation. For example, the cosmetic composition of the present invention may be formulated with a vehicle into cream, lotion, tonic, spray, aerosol, oil, solution, suspension, gel, ointment, emulsion, paste, or hair tonic. The pharmaceutical or cosmetic formulations may be prepared using any apparatus or method well known in the art (refer to Remington's Pharmaceutical Science, latest version).

In the composition of the present invention, a base may be properly combined with, for example, a cosmetically acceptable additive. So long as it is accepted in the art, any base may be used in the composition. Exemplary among them are distilled water, mineral water, ethanol, glycerin, squalene, 1,3-propyleneglycol, 1,3-butyleneglycol, castor oil, tsubaki oil, and liquid petrolatum. Examples of the additive include a surfactant, an emulsifier, a thickener, a preservative, an antioxidant, and a flavorant, but are not limited thereto. The surfactant may be cationic, anionic or non-ionic. Examples of the cationic surfactant include alkaline salts of higher fatty acids such as lauric acid, myristic acid, palmitic acid, stearic acid and oleic acid (e.g., sodium, potassium, ammonium, triethanolamine salt); esters of alkyl sulfonic acid such as sodium laurylsulfate, and triethanol amine laurylsulfonate; and alkyl ether sulfonate esters such as sodium polyoxyethylene laurylether sulfonate and triethanolamine polyoxyethylene laurylether sulfonate. Included among the non-ionic surfactants are polyoxyethylene alkyl ethers such as polyoxyethylene laurylether and polyoxyethylene oleylether; and alkanolamine such as coconut fatty acid diethanolamide and diethanolamide laurate. Stearyl trimethyl ammonium chloride, cetyl trimethyl ammonium chloride and stearyl bis(diethylalcohol)hydroxy ethyl ammonium chloride are examples of the anionic surfactants.

Examples of the emulsifier include cetanol, stearyl alcohol and behenyl alcohol. Examples of the thickener include sodium alginate, methyl cellulose, carboxymethyl cellulose, polyvinyl alcohol and polyvinyl pyrrolidone.

Examples of the preservative include ethyl parahydroxybenzoate, butyl parahydroxybenzoate and benzalkonium chloride. Examples of the antioxidant include butyl hydroxytoluene, propyl galate and butyl hydroxyanisole. The flavorant may be perfume for general use and may be exemplified by citrus, lavender and floral.

Various factors including the patient's sex, age and health state, the severity of disease, etc., must be considered in determining the quantity of a dose and the number of doses of the composition according to the present invention.

The antibiotically active, cosmetic composition comprising flufenamic acid, flufenamic acid derivative, flufenamic acid isomer, or flufenamic acid salt in according to the present invention may further comprise an antibiotic inhibitory of Gram-positive bacteria. Any antibiotic, if approved for use in inhibiting Gram-positive bacteria, may be used in the composition of the present invention. Preferred examples of the antibiotic include norfloxacin, oxacillin and cephalothin, but are not limited thereto.

Advantageous Effects

Because the inhibition mechanism used is different from those of conventional antibiotics, flufenamic acid can exert inhibitory activity effectively on bacteria resistant to conventional antibiotics. This novel antibiotic may be used alone or in combination with a conventional antibiotic. In the latter case, high therapeutic effects can be obtained at a low dose, with the concomitant reduction of side effects and toxicity. Because its intrinsic medical efficacy is newly discovered, the antibiotic of the present invention, which has been used as an anti-inflammatory drug, does not need to undergo separate clinical trials for the FDA's approval, thus remarkably reducing the time and cost of drug development and having a great advantage in market entry.

DESCRIPTION OF DRAWINGS

FIG. 5 shows comparison of sequence alignments of AKR1C3 (SEQ ID NO: 8), SA0658 (SEQ ID NO: 1), SA1606 (SEQ ID NO: 2), SA2001 (SEQ ID NO: 3), and 2,5-diketo-D-gluconate reductase A.

FIG. 9 shows enzymatic activities of AKR on methylglyoxal in the presence and absence of FLF, confirming the inhibitory activity of FLF against SaAKRs.

MODE FOR INVENTION

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLES

Example 1

Bacterial Strain

CCARM3080, a clinically identified species of methicillin-resistant *S. aureus* (MRSA), was purchased from the Culture Collection of antibiotic Resistant Microbes (www.ccarm.or.kr) and used for screening compounds. *Listeria monocytogenes* (KCTC3586), *Staphylococcus epidermidis* (KCTC1917) and *Bacillus subtilis* (KCTC2217) were obtained from the Korean Collection for Type Cultures (http://kctc.kribb.re.kr). *Enterococcus faecium* was granted from Dr. Ko, K. S. Sungkyunkwan University.

Example 2

Identification of Novel Compounds

To screen compounds having inhibitory activity against bacteria, MRSA was 200-fold diluted in 0.2 mL of LB in 96-well microplates and cultured overnight at 37° C. with agitation at 180 RPM. Prestwick chemical library was added at a final concentration of 100 μg/mL per well. The microplates were incubated at 37° C. for 24 hours with agitation at 180 RPM and the optical density at 600 nm was measured.

Figure 1:
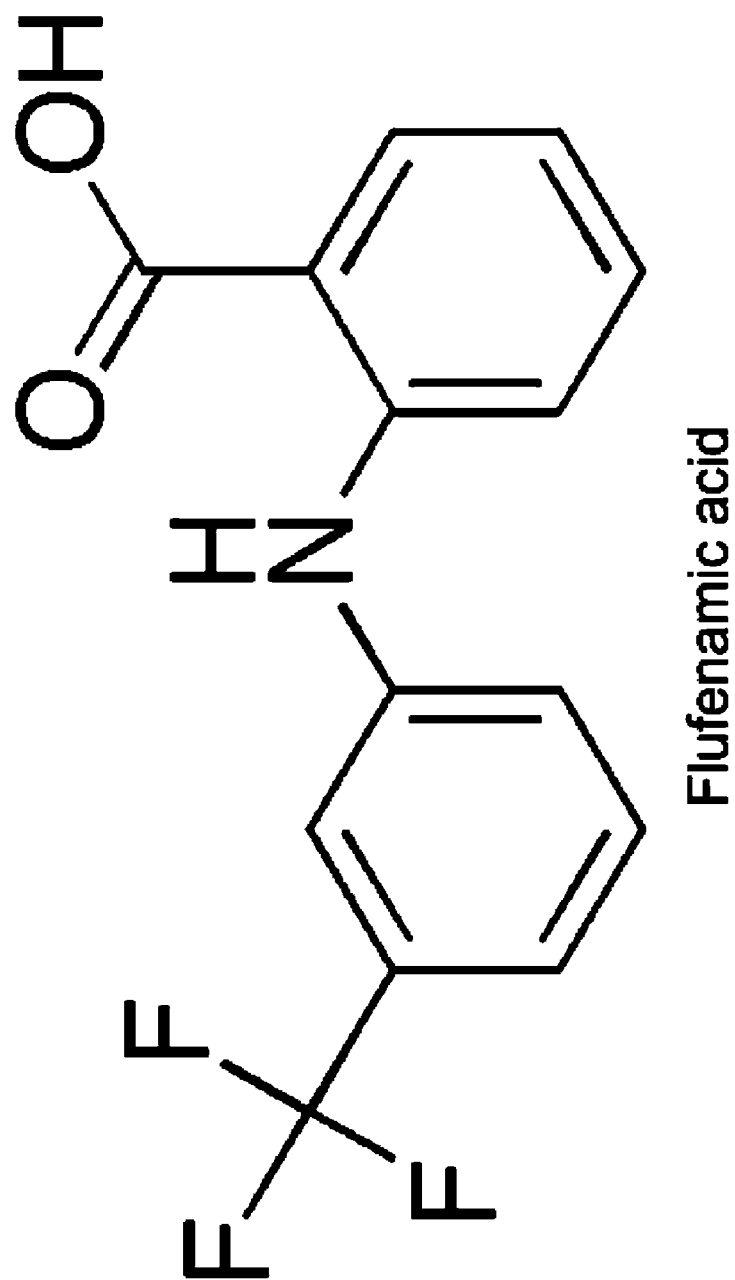
FIG. 1 shows a chemical structure of flufenamic acid.

Of the candidate compounds, flufenamic acid (FLF), shown in FIG. 1, was identified to be the most inhibitory of the bacteria.

Example 3

Assay for Inhibition against Methicillin-Resistant *Staphylococcus aureus*

FLF was assayed for inhibitory activity against Methicillin-resistant *staphylococcus aureus* (MRSA). In this regard, Methicillin-resistant *Staphylococcus aureus* (MRSA) was cultured overnight and 200-fold diluted in 2 mL of LB containing various concentrations of FLF. After additional incubation at 37° C. for 8 hours, cell densities were measured by recoding OD at 600 nm.

Figure 2:
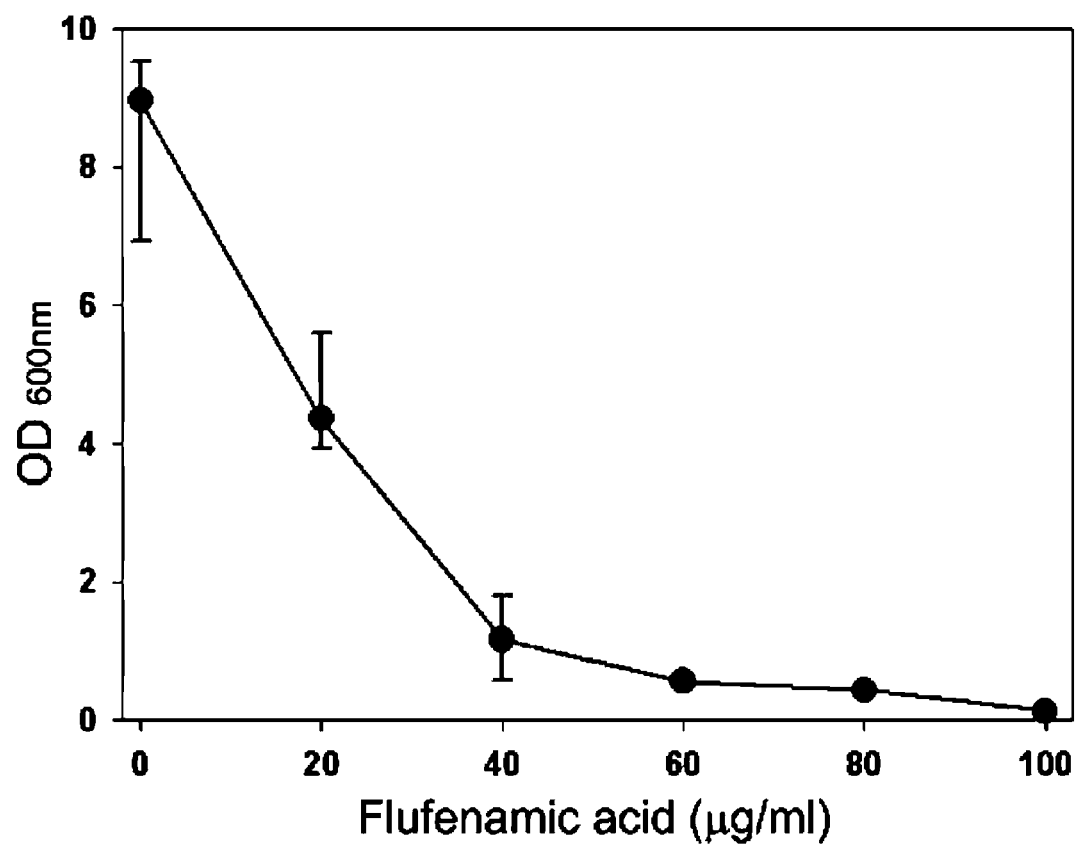
FIG. 2 shows inhibitory concentrations of flufenamic acid against *Staphylococcus aureus*.

As can be seen in FIG. 2 and Table 1, the growth of MRSA was 90% inhibited after incubation with 40 μg/mL FLF for 8 hours (FIG. 2) and the MIC of FLF against MRSA was found to be 64 μg/mL when measured after 24 hours of incubation (Table 1).

Example 4

Assay for Inhibition against *Staphylococcus epidermidis*, *Bacillussubtilis*, *Listeria monocytogenes*, and *Enterococcus faecium*

FLF was examined for inhibitory activity against various bacteria. *Staphylococcus epidermidis*, *Bacillus subtilis*, *Listeria monocytogenes* and *Enterococcus faecium* were cultured overnight and 200-fold diluted in 2 mL of LB containing various concentrations of FLF. Cell densities were determined by measuring the OD at 600 nm after incubation at 37° C. for 8 hours. The MICs of FLF were determined using a broth dilution method. In brief, bacteria were inoculated into LB containing serially diluted concentrations of FLF in 96-well microplates. After 24 hours of incubation, bacterial growth was examined. Antibacterial activity of FLF was tested over various Gram-positive bacteria including *Staphylococcus epidermidis*, *Bacillus subtilis*, *Listeria monocytogenes*, and *Enterococcus faecium*.

TABLE 1

| MICs of Flufenamic Acid against Gram-Positive Bacteria | |
| --- | --- |
| Bacteria | MICs (μg/ml) |
| S. aureus MSSA | 64 |
| S. aureus MRSA | 64 |
| S. epidermidis | 64 |
| B. subtilis | 32 |
| L. monocytogenes | 32 |
| E. faecium | 32 |

Figure 3:
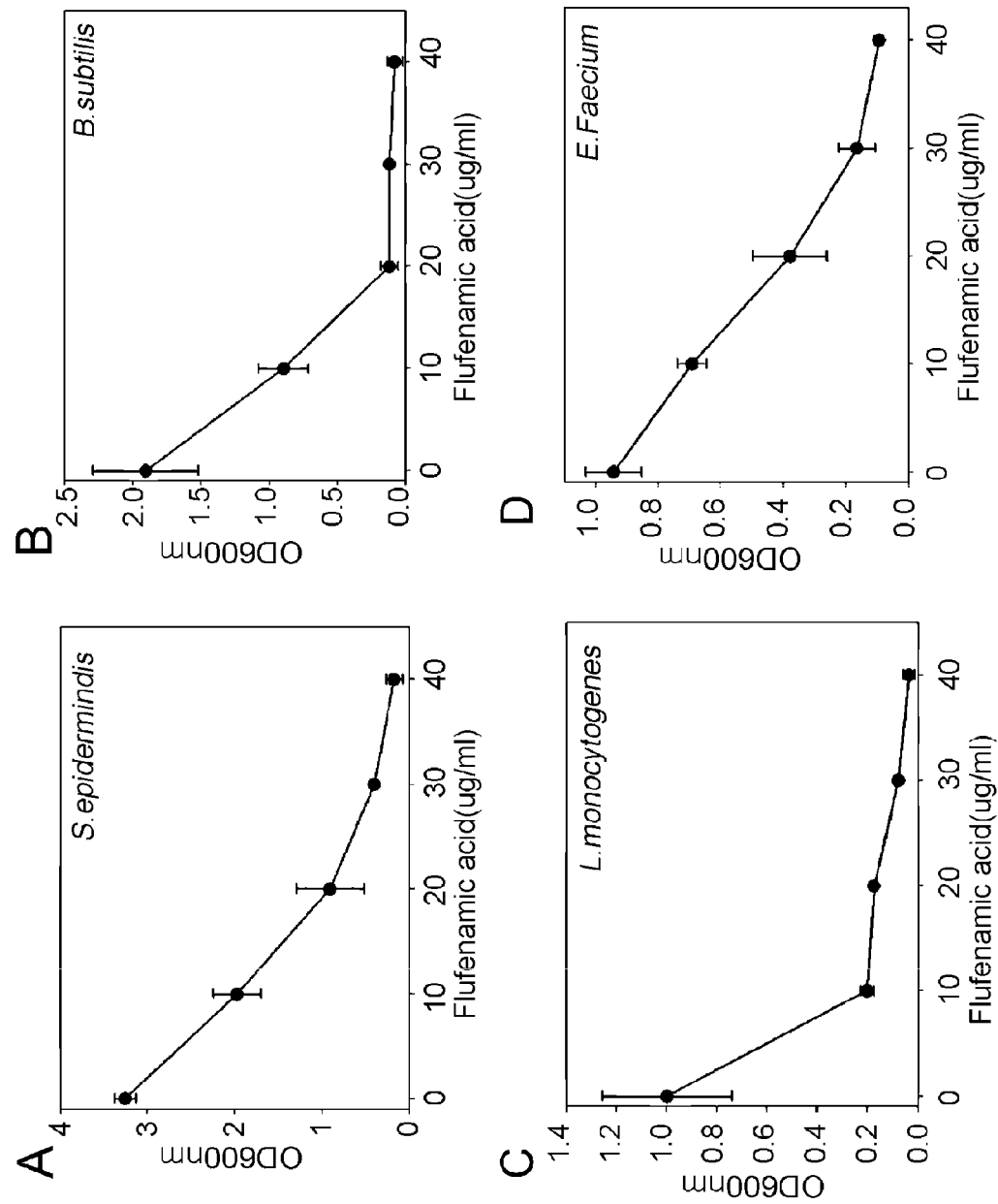
FIG. 3 shows inhibitory concentrations of flufenamic acid against *Staphylococcus epidermidis, Bacillus subtilis, Listeria monocytogenes* and *Enterococcus faecium*.

As shown in FIG. 3 and Table 1, *Staphylococcus epidermidis*, *Bacillus subtilis*, *Listeria monocytogenes*, and *Enterococcus faecium* were susceptible to FLF. Their growth was 90% inhibited after incubation with 20~40 μg/mL FLF for 8 hours (FIG. 3). The MICs of FLF against these bacteria were found to range from 32 to 64 μg/mL when measured after 24 hours of incubation (Table 1).

Example 5

Synergistic Effect of FLF with Other Antibiotics

To examine the synergistic effect of FLF with other antibiotics, Methicillin-resistant *Staphylococcus aureus* (MRSA) was cultured overnight and 200-fold diluted in 2 mL of LB containing 20 μg/ml FLF together with 0, 10, 20, 30, or 40 μg/ml Norfloxacin, Oxacillin or Cephalocin. Cell densities were determined by measuring OD at 600 nm after incubation at 37° C. for 8 hours.

TABLE 2

MICs of Antibiotics against MRSA in the Presence of Flufenamic Acid

| Antibiotics (mg/ml) | MICs (μg/ml) | | | | |
|---|---|---|---|---|---|
| | No FLF | 10 μg/ml FLF | 20 μg/ml FLF | 30μg/ml FLF | 40 μg/ml FLF |
| Norfloxacin | 128 | 64 | 32 | 16 | 8 |
| Oxacillin | >256 | 256 | 128 | 32 | 8 |
| Cephalothin | 128 | 128 | 64 | 16 | 4 |

Figure 4:
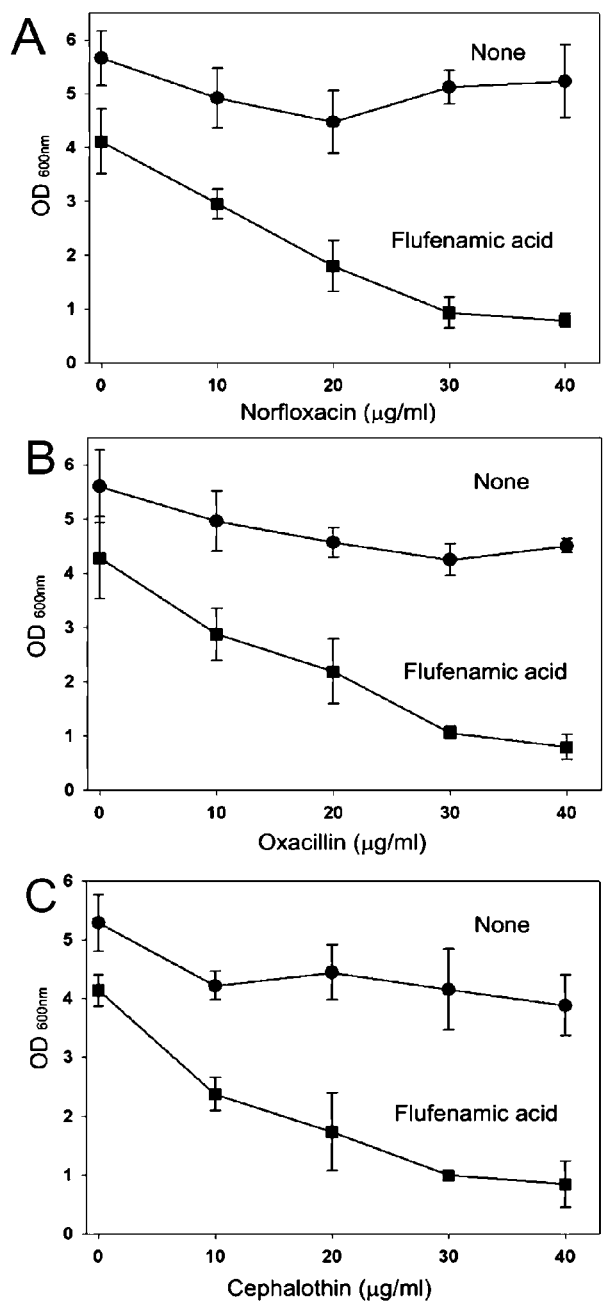
FIG. 4 shows inhibitory concentration of flufenamic acid used in combination with Norfloxacin, oxacillin, and cephalothin against *Staphylococcus aureus*.

As can be seen in Table 2 and FIG. 4, the MIC of Norfloxacin, a representative quinolone antibiotic targeting DNA gyrase, was reduced from 128 to 32 μg/ml in the presence of 20 μg/ml FLF (FIG. 4A). Similarly, FLF allows MRSA to be far more susceptible to oxacillin (FIG. 4B) and cephalothin (FIG. 4C), both β-lactam antibiotics targeting the biosynthesis of the cell wall. When used in combination with classical antibiotics, FLF synergistically inhibited MRSA infection and thus showed effective therapeutic effects (Table 2).

Example 6

Analysis of Bacterial Target Protein of Flufenamic Acid Using Bioinformation In order to identify the bacterial protein target of FLF, human AKR1C3, known as a protein to be associated with FLF, was compared with a library or database of sequences using the BLAST bioinformatics program.

As shown in FIG. 5, a Blast search identified ORFs—SA0658, SA1606, and SA2001 as being comparable with the sequence of human AKR1C3. The AKR analogs were found to share sequence homology of 34, 36 and 31%, respectively, with AKR1C3. In addition, these three proteins showed sequence homology of 41~45% with 2,5-diketo-D-gluconate reductase A (DkgA), one member of the AKR family. To examine whether FLF is associated with the ORFs (SA0658, SA1606, and SA2001) identified in S. aureus MRSA, DkgA of E. coli the three-dimensional structure of which had been established was used as a template for remodeling the three-dimensional structures of the proteins of interest. Primary modeling was performed with DS MODELLER, followed by optimization using the protocol of Discovery Studio (Accelrys, Inc). The models thus built were qualitatively checked using PROCHECK. Sequence alignments among AKR1C3, SA0658, SA1606, SA2001, and DkgA were established using the CLUSTALW program with a default parameter.

Figure 6:
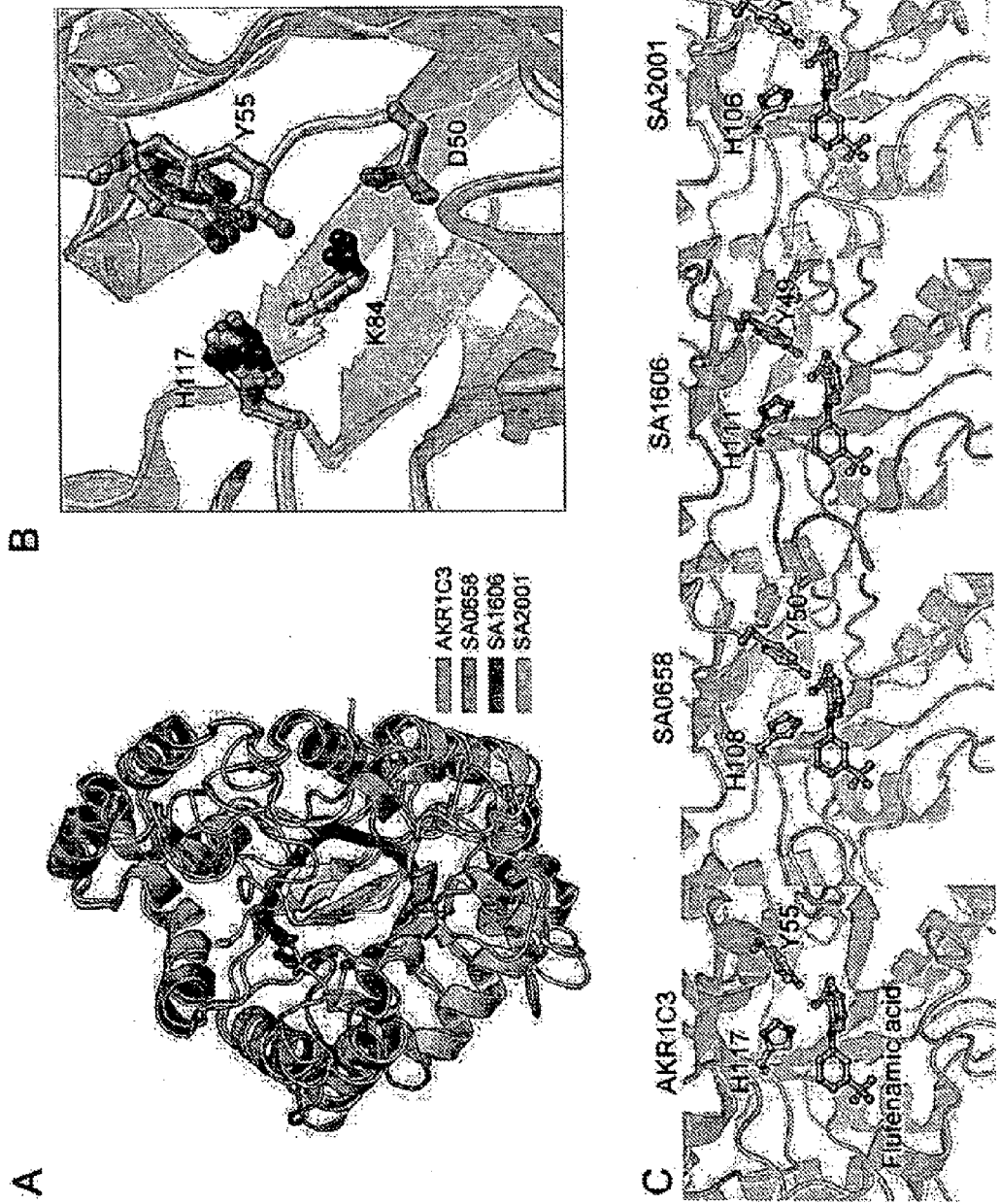
FIG. 6 shows three-dimensional structures and essential residues of AKR1C3, SA0658, SA1606, and SA2001.

As can be seen in FIG. 6, analysis of the crystal structure of human AKR1C3 complexed with FLF exhibited that FLF binds to the active site of AKR1C3. The inhibitory activity of FLF is due to the occupation of the oxyanion hole of AKR1C3 having a carboxylic group by FLF through hydrogen bonds with His117 and Tyr55 (FIG. 6). Each of the three AKR analogs SA0658, SA1606 and SA2001, identified in S. aureus, has four essential residues Asp50, Tyr55, Lys84, and His117, which are highly conserved in the AKR family and play an important role in enzymatic activity.

Analysis results showed that SaAKRs were significantly similar to human ARK1C3 in entire structure (FIG. 6A) as well as active site structure (FIG. 6B) and that the docking of FLF into the active site was successfully achieved (FIG. 6C). In this docking model, the oxygen atoms of the carboxylic acid group form hydrogen bonds with Tyr49 and His111, allowing FLF to occupy the oxyanion hole of the active site. Consequently, the three AKR analogs SA0658, SA1606 and SA2001, identified in S. aureus, were observed to have the same structure and working mechanism as those of ARK.

Example 7

Identification of the Binding of FLF to Target Proteins SA1606 and SA2001 by Gene Cloning and Protein Purification To examine the practical binding affinity of FLF for S. aureus protein targets (SA0658, SA1606, SA2001) and inhibitory activity against S. aureus, the targets were cloned. In the case of SA0658, although it was cloned and expressed, experiments could not be completed because the expressed protein precipitated.

Figure 7:
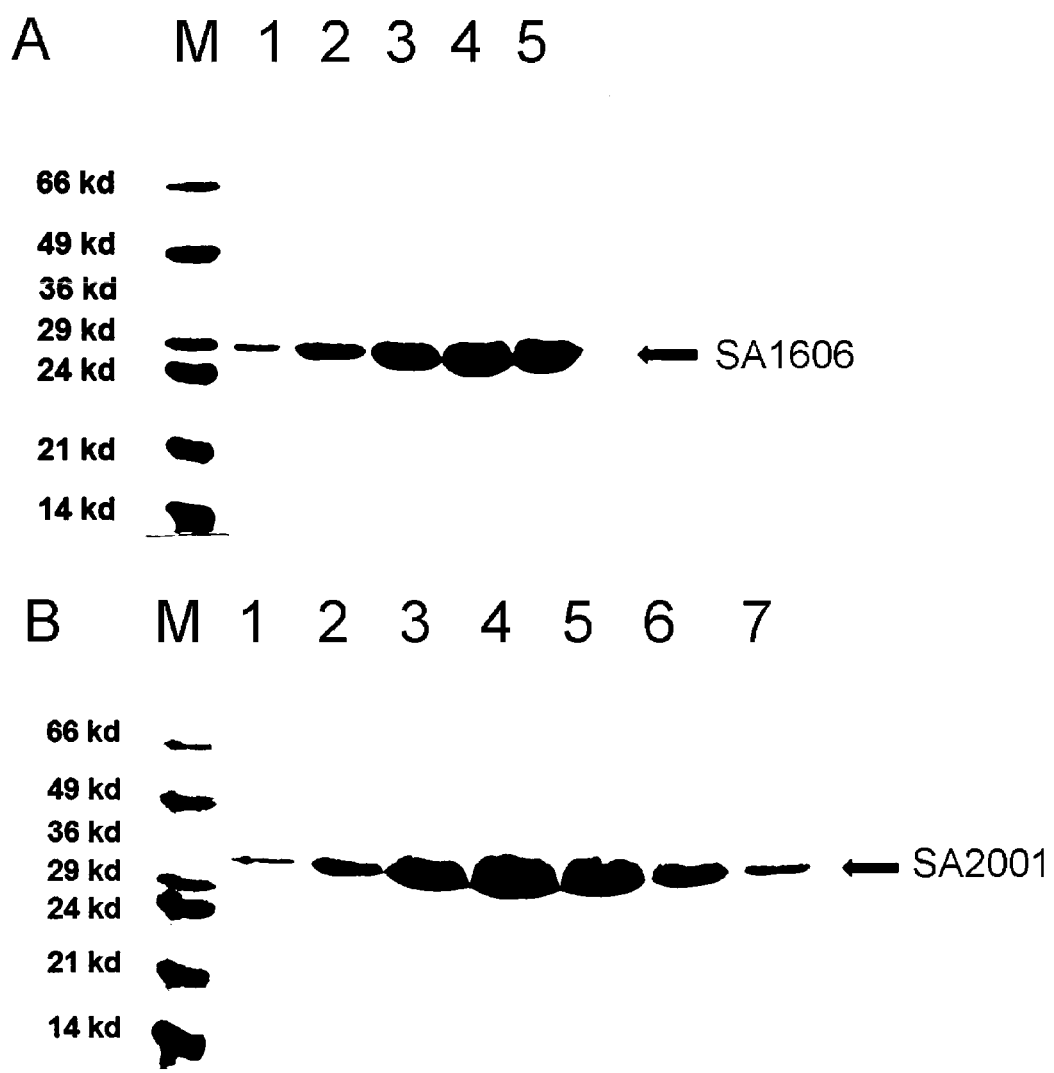
FIG. 7 shows purification of recombinant proteins (SA1606 and SA2001) for examining the function of SaAKRs.

Genes of SA1606 (GenBank number: BAB42874) and SA200125 (GenBank number: BAB43292) were amplified using PCR with the genomic DNA of S. aureus N315 serving as a template. PCR primers were 5'-GCGCGCGCCATG-GAGGTT AAAACATTTTAT-3' (SEQ ID NO: 4) and 5'-CG-GCGCCTCGAGTCCTTCAAAAGTTTTTGG-3' (SEQ ID NO: 5) for SA1606, and 5'-GCGCGCGCCATGGATCATAT-TGAAATAAGT-3' (SEQ ID NO: 6) and 5'-5 CGGCGCCTC-GAGTTCTCTGCTTGTAAGTGC-3' (SEQ ID NO: 7) for SA2001. NcoI and XhoI restriction sites were incorporated into the forward primer sequences and the reverse primer sequences, respectively. The PCR products were digested with NcoI and XhoI and inserted into NcoI/XhoI-digested pET28a vectors (Novagen). The DNAs 10 thus ligated were transformed into E. coli BL21 DE3 (Invitrogen). Coding sequences of the cloned genes SA1606 and SA2001 were confirmed by nucleotide sequencing. Recombinant SA1606 and SA2001 with histidine tag at the C-terminus were expressed in E. coli and then loaded into Hi-Trap chelating 15 columns (GE Healthcare) equilibrated with buffer A (20 mM HEPES, pH 7.5, 50 mM imadazole and 500 mM NaCl). The bound proteins were eluted with a linear gradient of 0.01-0.5 M imidazole in buffer A. Active fractions were concentrated and gel filtrated using a Superdex 200 column (GE Healthcare) in a 20 buffer containing 20 mM HEPES (pH 7.5) and 2 mM DTT. The purified proteins are as shown in FIG. 7.

Example 8

Evaluation of Binding Affinity of FLF for Target Proteins by Isothermal Titration calorimetry Binding affinity for SA1606 and SA2001 of FLF was measured using VP-ITC Micro calorimeter (MicroCal Inc). All of the proteins and FLF were prepared in 10 mM HEPES, pH 7.0 and 3% DMSO, followed by removing gas from the samples. In each titration experiment, 8 μl of FLF was injected into 1.5 mL of sample cells containing the proteins 20~30 times at regular intervals of 4 min. Thereafter, the affinity of FLF for the proteins were calculated on the basis of the heat generated upon the binding of FLF to the proteins. The data was analyzed with ORIGIN software (MicroCal Inc).

Figure 8:
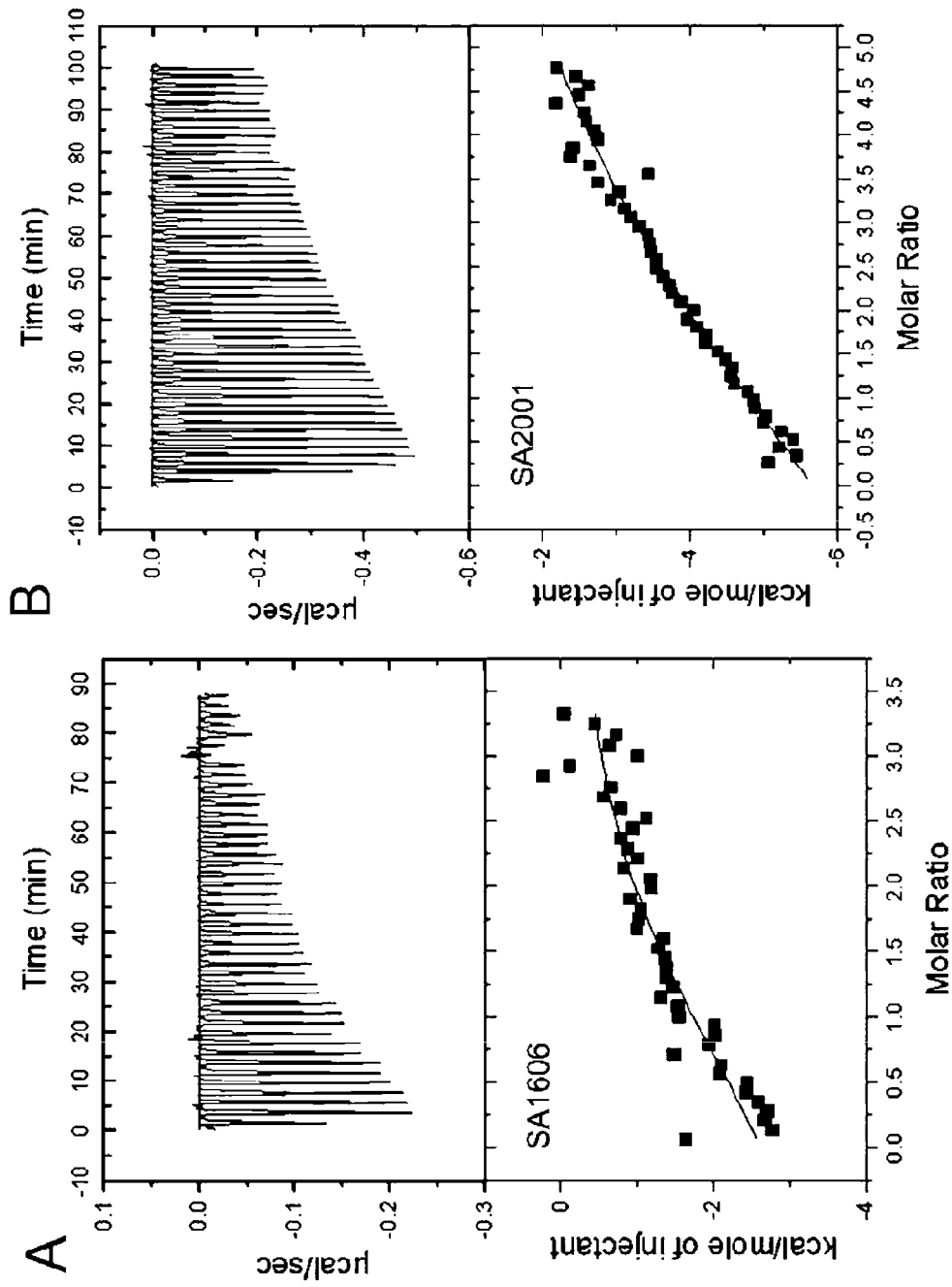
FIG. 8 shows binding affinity of FLF for SA1606 and SA2001.

As is apparent form the data of FIG. 8, dissociation constants (Kd) between FLF and SA1606 and between FLF and SA2001 were 14.5 μM and 38.1 μM, respectively, indicating that FLF can practically bind to SA1606 and SA2001 and that the protein targets of FLF in S. aureus MRSA are SA1606 and SA2001.

Example 9

Enzymatic Assay for Inhibitory Activity of FLF Against Protein Targets

Aldo-keto reductase (AKR) activity was measured to examine whether FLF inhibits the enzymatic activities of SA1606 and SA2001 on the basis of the data of Example 8 showing the binding of FLF to SA16006 and SA2001. On the whole, bacterial AKR catalyzes the reduction of various chemicals with NADPH. Hence, the enzymatic activity of AKR can be determined by monitoring the absorbance of NADPH at 340 nm. As is evidenced in Example 6, SA1606 and SA2001 have structural and functional similarity with the human aldo-keto reductase AKR1C3 and the bacterial aldo-keto reductase DkgA. Thus, the enzymatic activity of DkgA was measured to analyze the inhibitory activity of FLF. The reaction for evaluating enzymatic activity was comprised of 0.5 mM NADPH, 5 mM methylglyoxal and 10 µM aldo-keto reductase in 50 mM sodium phosphate buffer, pH 7.0. Absorbance at 340 nm of the reaction was measured for 10 min to calculate the consumption of NADPH.

As can be seen in FIG. 9, SA1606 and SA2001 reduced methylglyoxal with NADPH (yellow lines), but the enzymatic activity was inhibited in the presence of FLF (brown lines), demonstrating that FLF is bound directly to the active sites of the enzymes SA1606 and SA2001, thus inhibiting the enzymatic activity of the *S. aureus* aldo-keto reductase.

FORMULATION EXAMPLES

A better understanding of the present invention may be obtained through the following formulation examples of the antibiotically active, pharmaceutical or cosmetic composition comprising flufenamic acid, flufenamic acid derivative, flufenamic acid isomer, or flufenamic acid salt which are set forth to illustrate, but are not to be construed as the limit of the present invention.

EXAMPLES OF COSMETIC FORMULATION

Formulation Example 1

Skin Lotion (Content: wt %)

The composition: 0.001
Glycerin: 3.0
Butylene glycol: 2.0
Propylene glycol: 2.0
Carboxyvinyl polymer: 0.1
Ethanol: 10.0
Triethanolamine: 0.1
Preservative, pigment, flavorant, distilled water: q.s
Total: 100.0

Formulation Example 2

Nutrient Cream (Content: wt %)

The composition: 0.001
Beeswax: 10.0
Polysorbate 60: 1.5
Sorbitan sesquiolate: 0.5
Liquid paraffin: 10.0
Squalane: 5.0
Caprilic/capric triglyceride: 5.0
Triethanolamine 0.2
Preservative, pigment, flavorant, distilled water: q.s.
Total: 100.0

Formulation Example 3

Hair Soap (Content: wt %)

The composition: 0.001
Titanium dioxide: 0.2
Polyethylene glycole: 0.8
Glycerin: 0.5
Ethylene diaminetetraacetic acid: 0.05
Sodium: 1.0
Pigment: q.s.
Soap flavor: q.s.
Cosmetic soap base (water content 13, wt parts): q.s.
Total: 100.0

EXAMPLES OF PHARMACEUTICAL FORMULATION

Formulation Example 1

Ointment

The composition: 3 g
Dexpanthenol: 1.5 g
Stearic acid: 1.0 g
Liquid paraffin: 5.0 g
Spermaceti: 4.0 g
Cetanol: 3.0 g
Propylene glycol: 13.0 g
Triethanolamine: 1.5 g
Dibutylhydroxytoluene: 0.025 g
Ethyl benzoate: 0.0225 g
Propyl benzoate: 0.015 g
Polysorbate: 0.1 g
Purified water: 65.0 g An ointment was prepared from these ingredients according to a conventional method.

The ointment was applied at a dose of 0.5~1 g twice a day constantly for 3~6 months to the lesion.

Formulation Example 2

Lotion

The composition: 1.0 g
Dexpanthenol: 1.5 g
Glycerin: 0.6 g
Hydroxypropylcellulose: 0.085 g
Beegum: 0.0255 g
Purified water: q.s.

A lotion was prepared from these ingredient according to a conventional method.

The lotion was applied at a dose of 0.1~1 mL twice a day constantly for 3~6 months to the lesion.

Formulation Example 3

Capsule

The composition: 10 g
Crystalline cellulose: 3 g
Lactose: 14.8 g
Magnesium stearate: 0.2 g These ingredients were mixed and loaded into gelatin capsules according to a conventional method to form capsules.

Formulation Example 4

Injection

The composition: 10 g
Mannitol: 180 g
Sterile water for injection: 2974 g
$Na_2HPO_4 \cdot 12H_2O$: 26 g These ingredients were dissolved to form a total volume of 2 liters according to a conventional method.

Formulation Example 5

Liquid

The composition: 20 mg
Isomerose: 10 g
Mannitol: 5 g
Purified water: q.s.

Using a conventional method, the ingredients were added to distilled water to which lemon flavor was then added in a suitable amount. After the ingredients were mixed, distilled water was added to bring the total volume to 100 mL, which was then loaded into a brown bottle and sterilized.

The invention claimed is:

1. An antibiotically active pharmaceutical composition, comprising (a) flufenamic acid of Chemical Formula (1), or flufenamic acid salt; and (b) an antibiotic selected from the group consisting of norfloxacin, oxacillin, and cephalothin, wherein a weight ratio of the antibiotic to flufenamic acid, or flufenamic acid salt is at least 0.5, and wherein the component (a) targets Gram-positive bacterial aldo-keto reductase

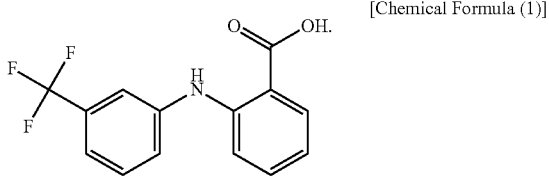 [SMILES: O=C(O)c1ccccc1Nc1cccc(C(F)(F)F)c1]

[Chemical Formula (1)]

2. The antibiotically active pharmaceutical composition of claim 1, wherein the Gram-positive bacteria is selected from the group consisting of *Staphylococcus aureus, Staphylococcus epidermidis, Bacillus subtilis, Listeria monocytogenes*, and *Enterococcus faecium*.

3. The antibiotically active pharmaceutical composition of claim 1, wherein the antibiotic-resistant bacteria is selected from the group consisting of MRSA (Methicillin-Resistant *Staphylococcus aureus*), VRSA (Vancomycin-Resistant *Staphylococcus aureus*), MRE (multiple-drug resistant enterococci), and VRE (Vancomycin-Resistant enterococci).

4. The antibiotically active pharmaceutical composition of claim 1, wherein the reductase has an amino acid sequence consisting of SEQ ID NO: 1.

5. The antibiotically active pharmaceutical composition of claim 1, wherein the reductase has an amino acid sequence consisting of SEQ ID NO: 2.

6. The antibiotically active pharmaceutical composition of claim 1, wherein the reductase has an amino acid sequence consisting of SEQ ID NO: 3.

7. A method of treating a Gram-positive bacterial infection, comprising administering a pharmaceutical composition of claim 1 to a patient having the Gram-positive bacteria infection.

8. The method of claim 7, wherein the Gram-positive bacteria is selected from the group consisting of *Staphylococcus aureus, Staphylococcus epidermidis, Bacillus subtilis, Listeria monocytogenes*, and *Enterococcus faecium*.

9. The method of claim 7, wherein the Gram-positive bacteria is selected from the group consisting of MRSA (Methicillin-Resistant *Staphylococcus aureus*), VRSA (Vancomycin-Resistant *Staphylococcus aureus*), MRE (multiple-drug resistant enterococci), and VRE (Vancomycin-Resistant enterococci).

10. The method of claim 7, wherein the reductase has an amino acid sequence consisting of SEQ ID NO: 1.

11. The method of claim 7, wherein the reductase has an amino acid sequence consisting of SEQ ID NO: 2.

12. The method of claim 7, wherein the reductase has an amino acid sequence consisting of SEQ ID NO: 3.

* * * * *

SEQUENCE LISTING

<160> NUMBER OF SEQ ID NOS: 8

<210> SEQ ID NO 1
<211> LENGTH: 279
<212> TYPE: PRT
<213> ORGANISM: Staphylococcus aureus

<400> SEQUENCE: 1

```
Met Leu Asn Glu Ile Gln Ile Leu Asn Asn Gly Tyr Pro Met Pro Ser
1               5                   10                  15

Val Gly Leu Gly Val Tyr Lys Ile Ser Asp Glu Asp Met Thr Lys Val
            20                  25                  30

Val Asn Ala Ala Ile Asp Ala Gly Tyr Arg Ala Phe Asp Thr Ala Tyr
        35                  40                  45

Phe Tyr Asp Asn Glu Ala Ser Leu Gly Arg Ala Leu Lys Asp Asn Gly
    50                  55                  60

Val Asp Arg Glu Asp Leu Phe Ile Thr Thr Lys Leu Trp Asn Asp Tyr
65                  70                  75                  80

Gln Gly Tyr Glu Lys Thr Phe Glu Tyr Phe Asn Lys Ser Ile Glu Asn
                85                  90                  95

Leu Gln Thr Asp Tyr Leu Asp Leu Phe Leu Ile His Trp Pro Cys Glu
            100                 105                 110

Ala Asp Gly Leu Phe Leu Glu Thr Tyr Lys Ala Met Glu Glu Leu Tyr
        115                 120                 125

Glu Gln Gly Lys Val Lys Ala Ile Gly Val Cys Asn Phe Asn Val His
    130                 135                 140

His Leu Glu Lys Leu Met Ala Gln Ser Ser Ile Lys Pro Met Val Asn
145                 150                 155                 160

Gln Ile Glu Val His Pro Tyr Phe Asn Gln Gln Glu Leu Gln Glu Phe
                165                 170                 175

Cys Asp Arg His Asp Ile Lys Val Thr Ala Trp Met Pro Leu Met Arg
            180                 185                 190

Asn Arg Gly Leu Leu Asp Asn Pro Val Ile Val Lys Ile Ala Glu Lys
        195                 200                 205

Tyr His Lys Thr Pro Ala Gln Val Val Leu Arg Trp His Leu Ala His
    210                 215                 220

Asn Arg Ile Ile Ile Pro Lys Ser Gln Thr Pro Lys Arg Ile Gln Glu
225                 230                 235                 240

Asn Ile Asp Ile Leu Asp Phe Asn Leu Glu Leu Thr Glu Val Ala Glu
                245                 250                 255

Ile Asp Ala Leu Asp Arg Asn Ala Arg Gln Gly Lys Asn Pro Asp Asp
            260                 265                 270

Val Lys Ile Gly Asp Leu Lys
        275
```

```
<210> SEQ ID NO 2
<211> LENGTH: 277
<212> TYPE: PRT
<213> ORGANISM: Staphylococcus aureus

<400> SEQUENCE: 2
```

Met Glu Val Lys Thr Phe Tyr Asn Gly Asn Thr Met Pro Gln Ile Gly
1               5                   10                  15

Leu Gly Thr Phe Arg Val Glu Asn Asp Glu Asn Cys Met Glu Ser Val
            20                  25                  30

Lys Tyr Ala Ile Glu Gln Gly Tyr Arg Ser Ile Asp Thr Ala Lys Val
        35                  40                  45

Tyr Gly Asn Glu Glu Gln Val Gly Ala Gly Ile Arg Ala Gly Leu Glu
    50                  55                  60

Ser Thr Gly Ile Ala Arg Glu Asp Leu Phe Ile Thr Ser Lys Leu Tyr
65                  70                  75                  80

Phe Glu Asp Phe Gly Arg Glu Asn Val Ala Ala Ala Tyr Glu Ala Ser
                85                  90                  95

Leu Ser Arg Leu Gly Leu Lys Tyr Leu Asp Leu Tyr Leu Val His Trp
            100                 105                 110

Pro Gly Thr Asn Glu Ala Val Met Val Asp Thr Trp Lys Gly Met Glu
        115                 120                 125

Asp Leu Tyr Lys Asn Asn Lys Ala Lys Asn Ile Gly Val Ser Asn Phe
    130                 135                 140

Glu Pro Glu His Leu Glu Ala Leu Leu Ala Gln Val Ser Ile Lys Pro
145                 150                 155                 160

Val Ile Asn Gln Val Glu Tyr His Pro Tyr Leu Thr Gln His Lys Leu
                165                 170                 175

Lys Leu Tyr Leu Ala Ala Gln His Ile Val Met Glu Ser Trp Ser Pro
            180                 185                 190

Leu Met Asn Ala Gln Ile Leu Asn Asp Glu Thr Ile Lys Asp Ile Ala
        195                 200                 205

Gln Glu Leu Gly Lys Ser Pro Ala Gln Val Val Leu Arg Trp Asn Val
    210                 215                 220

Gln His Gly Val Val Ile Ile Pro Lys Ser Val Thr Pro Asn Arg Ile
225                 230                 235                 240

Ser Glu Asn Phe Gln Ile Phe Asp Phe Glu Leu Ser Asp Gln Met
                245                 250                 255

Thr Arg Ile Asp Gly Leu Asn Gln Asp Lys Arg Ile Gly Pro Asp Pro
    260                 265                 270

Lys Thr Phe Glu Gly
        275

```
<210> SEQ ID NO 3
<211> LENGTH: 282
<212> TYPE: PRT
<213> ORGANISM: Staphylococcus aureus

<400> SEQUENCE: 3
```

Met Asn His Ile Glu Ile Ser Lys Asp Val Lys Ile Pro Val Leu Gly
1               5                   10                  15

Phe Gly Val Phe Gln Ile Pro Gln Glu Gln Thr Ala Glu Ala Val Lys
            20                  25                  30

Glu Ala Ile Lys Ala Gly Tyr Arg His Ile Asp Thr Ala Gln Ser Tyr
        35                  40                  45

```
Leu Asn Glu Thr Glu Val Gly Gln Gly Ile Glu Ala Ser Gly Ile Asp
 50                  55                  60

Arg Ser Glu Leu Phe Ile Thr Thr Lys Val Trp Ile Glu Asn Val Asn
 65                  70                  75                  80

Tyr Glu Asp Thr Ile Lys Ser Ile Glu Arg Ser Leu Gln Arg Leu Asn
                 85                  90                  95

Leu Asp Tyr Leu Asp Leu Val Leu Ile His Gln Pro Tyr Asn Asp Val
             100                 105                 110

Tyr Gly Ser Trp Arg Ala Leu Glu Leu Lys Glu Asn Gly Lys Ile
         115                 120                 125

Lys Ala Ile Gly Val Ser Asn Phe Gly Val Asp Arg Ile Val Asp Leu
130                 135                 140

Gly Ile His Asn Gln Ile Gln Pro Gln Val Asn Gln Ile Glu Ile Asn
145                 150                 155                 160

Pro Phe His Gln Gln Glu Gln Val Ala Ala Leu Gln Gln Glu Asn
                 165                 170                 175

Val Val Val Glu Ala Trp Ala Pro Phe Ala Glu Gly Lys Asn Gln Leu
             180                 185                 190

Phe Gln Asn Gln Leu Leu Gln Ala Ile Ala Asp Lys Tyr Asn Lys Ser
         195                 200                 205

Ile Ala Gln Val Ile Leu Arg Trp Leu Val Glu Arg Asp Ile Val Val
210                 215                 220

Leu Ala Lys Ser Val Asn Pro Glu Arg Met Ala Gln Asn Leu Asp Ile
225                 230                 235                 240

Phe Asp Phe Glu Leu Thr Glu Leu Asp Lys Gln Gln Ile Ala Thr Leu
                 245                 250                 255

Glu Glu Ser Asn Ser Gln Phe Phe Ser His Ala Asp Pro Glu Met Ile
             260                 265                 270

Lys Ala Leu Thr Ser Arg Glu Leu Asp Val
         275                 280

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgcgcgcca tggaggttaa aacatttttat                                      30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggcgcctcg agtccttcaa aagttttttgg                                      30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
gcgcgcgcca tggatcatat tgaaataagt                                        30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cggcgcctcg agttctctgc ttgtaagtgc                                        30

<210> SEQ ID NO 8
<211> LENGTH: 331
<212> TYPE: PRT
<213> ORGANISM: Homo sapiens

<400> SEQUENCE: 8

Met Asp Ser Lys Gln Gln Cys Val Lys Leu Asn Asp Gly His Phe Met
1               5                   10                  15

Pro Val Leu Gly Phe Gly Thr Tyr Ala Pro Glu Val Pro Arg Ser
            20                  25                  30

Lys Ala Leu Glu Val Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Thr Phe His Arg Pro Glu Leu Val Arg
                85                  90                  95

Pro Ala Leu Glu Asn Ser Leu Lys Lys Ala Gln Leu Asp Tyr Val Asp
            100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220

Lys Arg Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Gln Asn Val Gln Val Phe Glu Phe Gln Leu
        275                 280                 285
```

```
Thr Ala Glu Asp Met Lys Ala Ile Asp Gly Leu Asp Arg Asn Leu His
    290             295             300

Tyr Phe Asn Ser Asp Ser Phe Ala Ser His Pro Asn Tyr Pro Tyr Ser
305             310             315             320

Asp Glu Tyr Leu Glu His His His His His
            325             330
```